United States Patent [19]

Gethöffer et al.

[11] Patent Number: 5,279,757

[45] Date of Patent: Jan. 18, 1994

[54] STABLE PEROXYCARBOXYLIC ACID GRANULE COMPRISING AN IMIDOPEROXYCARBOXYLIC ACID OR SALT THEREOF

[75] Inventors: Hanspeter Gethöffer, Frankfurt am Main; Gerd Reinhardt, Kelkheim/Taunus; Gerhard Nöltner, Frankfurt am Main; Rüdiger Funk, Wiesbaden, all of Fed. Rep. of Germany

[73] Assignee: Hoechst Aktiengesellschaft, Frankfurt, Fed. Rep. of Germany

[21] Appl. No.: 958,602

[22] Filed: Oct. 6, 1992

Related U.S. Application Data

[63] Continuation-in-part of Ser. No. 680,325.

[30] Foreign Application Priority Data

Apr. 6, 1990 [DE] Fed. Rep. of Germany ....... 4011185

[51] Int. Cl.⁵ .................... C11D 3/395; C11D 7/54; C11D 9/42
[52] U.S. Cl. ...................... 252/95; 252/99; 252/102; 252/542; 252/546; 252/174.24; 252/186.25
[58] Field of Search ............... 252/95, 102, 542, 546, 252/186.25, 99, 174.24

[56] References Cited

U.S. PATENT DOCUMENTS

| | | | |
|---|---|---|---|
| 3,639,285 | 2/1972 | Nielson | 252/100 |
| 4,009,113 | 2/1977 | Green et al. | 252/95 |
| 4,126,573 | 11/1978 | Johnston | 252/99 |

FOREIGN PATENT DOCUMENTS

| | | |
|---|---|---|
| 0200163 | 11/1986 | European Pat. Off. . |
| 0256443 | 2/1988 | European Pat. Off. . |
| 0325288 | 7/1989 | European Pat. Off. . |
| 0349940 | 1/1990 | European Pat. Off. . |
| 0435379 | 7/1991 | European Pat. Off. . |
| 3636904 | 5/1988 | Fed. Rep. of Germany . |

OTHER PUBLICATIONS

English translation of EP-0349 940; Jan. 10, 1990.

Primary Examiner—Paul Lieberman
Assistant Examiner—Erin M. Higgins
Attorney, Agent, or Firm—Connolly and Hutz

[57] ABSTRACT

Stable peroxycarboxylic acid granules composed essentially of (1) an imidoperoxycarboxylic acid or its salts of the formula

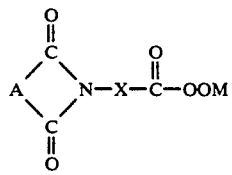

in which
A is a group of the formula

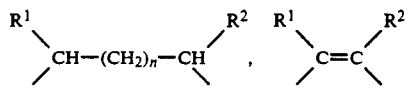

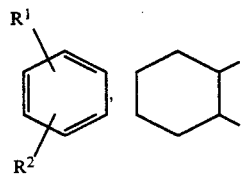

or

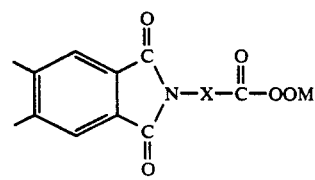

(Abstract continued on next page.)

n is the number 0, 1 or 2, $R^1$ is hydrogen, chlorine, bromine, $C_1$–$C_{20}$-alkyl, $C_1$–$C_{20}$-alkenyl, aryl or alkylaryl, $R^2$ is hydrogen, chlorine, bromine or a group of the formula —$SO_3M$, —$CO_2M$ or —$OSO_3M$, M is hydrogen, an alkali metal or ammonium ion or the equivalent of an alkaline earth metal ion, and X is $C_1$–$C_{19}$-alkylene or arylene, (2) an inorganic sulfate and/or phosphate salt and/or a non-oxidizable surfactant as granulating auxiliaries and (3) a homo- or copolymer of (meth)acrylic acid or its salts or a copolymer of (meth)acrylic acid or its salts and other carboxylic acids polymerizable therewith as a film-forming coating substance.

12 Claims, No Drawings

STABLE PEROXYCARBOXYLIC ACID GRANULE COMPRISING AN IMIDOPEROXYCARBOXYLIC ACID OR SALT THEREOF

This application is a continuation-in-part of application Ser. No. 07/680,325 filed on Apr. 4, 1991, now abandoned.

The present invention relates to storage-stable, high-percentage bleach active compounds in granulated form, which contain solid imidoperoxycarboxylic acids as bleaching components. The granules according to the invention can be employed as bleaching additives or oxidants in detergents, cleaning agents and disinfectants.

Inorganic persalts such as sodium perborate or percarbonates are long-known as bleaching agent additives in detergents. However, they display their optimum bleaching power only at temperatures above 60° C. For their activation, a number of organic compounds are described which, during the washing process, release a peroxycarboxylic acid with hydrogen peroxide. This has a bleaching effect even at temperatures below 60° C. The best-known example of these is tetraacetylethylenediamine (TAED).

Additionally, however, more recently a number of peroxycarboxylic acids for direct use in detergents have been described.

However, a problem both with the activators and with the previously prepared peroxycarboxylic acids is their low storage stability in alkaline detergent formulations. An adequate storage stability can only be achieved with these substances by a suitable granulating or coating process.

Known granulating auxiliaries for the most frequently used persalt activator tetraacetylethylenediamine are, for example, carboxymethylcellulose or ethoxylates of longer-chain alcohols.

More reactive persalt activators such as phthalic anhydride, on the other hand, require a more effective protection. Thus, to prepare storage-stable granules, previously prepared activator granules, composed of phthalic anhydride and a carrier material, are coated with a coating material composed of polymeric organic compounds such as polyacrylamide, copolymers of acrylic cellulose ethers (U.S. Pat. No. 4,009,113).

The stabilization of other sensitive detergent components (enzymes or percarbonates) by coating with polymeric materials meanwhile belongs to the prior art.

A particular problem, however, even nowadays is still the stabilization of reactive peroxycarboxylic acids. In the presence of basic detergent constituents, perfumes and enzymes, redox reactions easily occur with the loss of active oxygen. In addition, oxidation reactions can very easily occur in which valuable detergent components such as perfumes or enzymes are destroyed by oxidation.

A number of proposals have been made to solve the problem.

Thus, EP 200,163 describes granules of uniform composition, comprising 3-50% of an aliphatic peroxycarboxylic acid, 40-90% of a hydratable inorganic salt and 0.2-10% of an organic polymer compound such as polyacrylic acid.

Granules having a particle size of 0.5 to 2 mm, composed of 20-65% of a peroxycarboxylic acid, 30-79.5% of an inorganic salt and 0.5-6.5% of a polymeric acid as a binder are described in EP 256,443. The product can be coated with a coating material in an additional reaction step and can thus be protected from reactions with oxidizable detergent constituents.

Analogous granules and their preparation are described in EP 272,402. In this case, previously prepared peroxycarboxylic acid granules are sprayed while agitating with an aqueous solution of a homo- or copolymer, which is soluble in alkaline medium, of an unsaturated organic carboxylic acid containing 3-6 carbon atoms and the mixture is simultaneously or subsequently dried. Preferred previously prepared granules are composed of 3-50 in particular 7-20%, of a peroxycarboxylic acid, $\alpha,\omega$-di-perdodecanoic acid, for its part, being preferred.

Granules composed of solid, preferably aliphatic, peroxycarboxylic acid particles which are coated with surface-active substances have additionally been described (German Offenlegungsschrift 2,737,864). To control an exothermic decomposition reaction, the coated peroxycarboxylic acid particles can also be combined with inorganic sulfates. Moreover, in order to protect the granules further, an additional coating of the granule core with acid-, ester-, ether- or hydrocarbon-containing substances can be carried out. These materials help in preventing moisture from reaching the peroxycarboxylic acid particles.

Patent Applications EP 200,163 and EP 272,402 particularly emphasize that the experience which has been obtained with one type of peroxycarboxylic acid can only rarely be transferred to another type. Optimum granules can therefore only be obtained by measures which are tailored to the particular type of peroxycarboxylic acid. Thus, it is known, for example, from U.S. Pat. No. 3,639,285 that surfactants favor the decomposition of peroxycarboxylic acids, whereas in German Offenlegungsschrift 2,737,864, they can be employed without problems as granulating auxiliaries.

In most of the granules described hitherto, $\alpha,\omega$-di-perdodecanoic acid (DPDDA) is employed as the organic peracid. Because of its thermal instability, it can only be converted in desensitized form into storage-stable granules having a content up to 30%.

Storage-stable granules of more reactive peracids having active contents of above 60% have hardly been described hitherto and place high demands on the granulating technique.

Using the imidoperoxycarboxylic acids (EP 325,288 and 349,940), a group of peroxycarboxylic acids was developed which have a distinctly higher oxidizing and bleaching power than $\alpha,\omega$-di-perdodecanoic acid. Economically and in terms of application technology, $\epsilon$-phthalimidoperoxycaproic acid (PAP) is of particular interest.

It was the aim of the present invention to convert this class of compounds into suitable storage-stable granules having active contents of at least 60%.

The object is achieved by agglomerating the imidoperoxycarboxylic acid with a granulating auxiliary in a mixer and then coating the agglomerate with a film-forming agent. The use of agents for the thermal stabilization of the peracid can be dispensed with in this case.

The invention therefore relates to storage-stable peroxycarboxylic acid granules, composed essentially of an imidoperoxycarboxylic acid or its salts of the formula

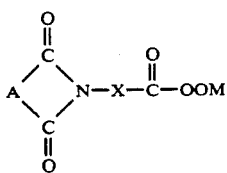

in which A is a group of the formula

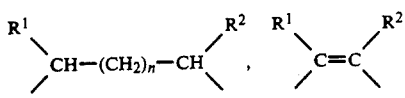

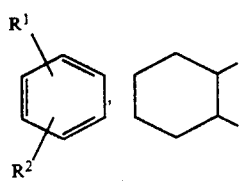

or

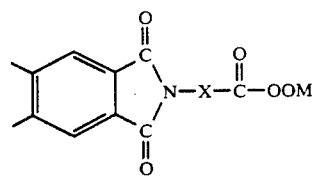

n is the number 0, 1 or 2,
R$^1$ is hydrogen, chlorine, bromine, C$_1$-C$_{20}$-alkyl, C$_1$-C$_{20}$-alkenyl, aryl, preferably phenyl, or alkylaryl, preferably C$_1$-C$_4$-alkylphenyl,
R$^2$ is hydrogen, chlorine, bromine or a group of the formula —SO$_3$M, —CO$_2$M or —OSO$_3$M,
M is hydrogen, an alkali metal or ammonium ion or the equivalent of an alkaline earth metal ion, and
X is C$_1$-C$_{19}$-, preferably C$_3$-C$_{11}$-alkylene, or arylene, preferably phenylene,
an inorganic sulfate and/or phosphate salt and/or a non-oxidizable surfactant as granulating auxiliaries and a homo- or copolymer of (meth)acrylic acid or its salts or a copolymer of (meth)acrylic acid or its salts and other organic carboxylic acids polymerizable therewith as a film-forming coating substance.

The three essential components of the bleaching agent according to the invention are therefore a peroxycarboxylic acid from the imidoperoxycarboxylic acid group, a granulating auxiliary and the coating agent. These are described, together with components to be used alternatively, in the following.

The Peroxycarboxylic Acid

Suitable peroxycarboxylic acids are the imidoperoxycarboxylic acids of the abovementioned formula. Preferred compounds of this formula are those in which
A is a group of the formula —CH$_2$—(CH$_2$)$_n$—CH$_2$— or —CH$_2$—CHR$^1$—,

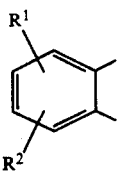

n is the number 0 or 1,
R$^1$ is hydrogen, C$_1$-C$_{20}$-alkyl or C$_1$-C$_{20}$-alkenyl,
R$^2$ is hydrogen or CO$_2$M
X is C$_3$-C$_{11}$-alkylene and
M is hydrogen, an alkali metal or ammonium ion or the equivalent of an alkaline earth metal ion.

Examples of preferred compounds of this type, which are employed in the granules according to the invention, are ε-phthalimidoperoxyhexanoic acid (PAP), ε-[dodecylsuccinimido] peroxyhexanoic acid, γ-phthalimidoperoxybutyric acid and ε-trimellitimidoperoxyhexanoic acid, their salts or their mixtures.

The imidoperoxycarboxylic acids can be prepared, for example, according to EP-349,940, for example by reaction of an anhydride of the formula

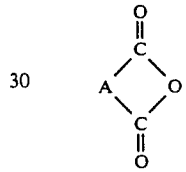

with amino acids of the formula

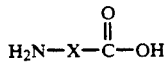

and oxidation of the imidocarboxylic acid obtained in this way with hydrogen peroxide in the presence of a strong acid. According to one variant of this process, the anhydride can also be reacted under pressure with a lactam in the presence of water.

The concentration of these peracids in the granules is at least in an amount greater than 65, preferably in an amount greater than 65 up to 90%.

The imidoperoxycarboxylic acids employed for granulation are normally solids at room temperature having a melting point of above 60° C. They can be employed for granulation in powder form, and in the dry or moist state.

The Granulating Auxiliary

The granulating auxiliaries have the object of forming a mechanically stable granule core and thus the basic structure of the actual granules by agglomeration with the peroxycarboxylic acid.

The granulating auxiliaries to be used according to the invention can be divided into two groups: a) inorganic sulfates and/or phosphates and b) organic compounds having surface-active properties (surfactants). The assumption is that these substances cannot be oxidized by the peracid.

Suitable inorganic sulfates/phosphates for the granules are sulfates/phosphates of alkali metals or alkaline earth metals, which are easily water-soluble and after dissolution have a neutral or acidic reaction. Sodium sulfate, sodium hydrogen sulfate, potassium sulfate, potassium hydrogen sulfate, sodium dihydrogen phosphate or magnesium sulfate are preferably used. Mixtures of the salts can additionally be employed.

Water-soluble anionic sulfates or sulfonates or zwitterionic surfactants are preferably employed as surface-active substances. Examples of compounds of this type are alkali metal or alkaline earth metal salts of alkyl-sulfates or -sulfonates having an alkyl group of 9 to 22 carbon atoms, which are obtained from natural or synthetically prepared fatty alcohols, or from hydrocarbons such as, for example, paraffin. Other useful surfactants which can be used are salts of alkylbenzenesulfonates in which the alkyl group contains 9 to 22 carbon atoms and can be branched or unbranched. All said compounds can optionally carry ethoxylated groups in the molecule. Preferred compounds are sec. alkanesulfonates, (Hostapur ®SAS), alkylsulfates and alkylbenzene-sulfonates.

The substances can be employed in solid or pasty form or as a solution for granulation. The preferred solvent is in this case water.

Mixtures of the granulating auxiliaries of group a) can be employed in any ratio with those of group b) for the granulation.

The amount of the granulation auxiliary in the finished granules is 5 to 39, preferably 15 to 35% by weight.

The Film-forming Coating Substance

Polymers of (meth)acrylic acid or copolymers of these acids with other unsaturated organic carboxylic acids are used as a film-forming coating substance. These compounds can also be employed in partly neutralized form. It is important, however, that the pH of the compounds is or is adjusted to between 2.5 and 7. Possible polymers are, for copolymers of acrylic acid or methacrylic acid with maleic acid, fumaric acid or itaconic acid. The compounds have an average molecular weight of 800–2,000,000, preferably 2,000–500,000.

The polymeric film-forming agents are preferably applied to the granule core in aqueous solution. Their concentration in the solution is 5–50%, preferably 10–30%.

The amount of the film-forming substance in the granule is 1 to 15, preferably 3–12%.

Additional Components

In some cases, it may be desirable that the granules according to the invention contain certain additional components. Examples of these are chelate-forming systems, dyes and agents for regulating the pH.

It is known that metal ions are capable of catalytically decomposing organic or inorganic percompounds. To overcome this problem, up to 3% of a chelating agent can be added to the granules. Preferred compounds are inorganic or organic phosphates or phosphonates or aminomethylenecarboxylic acids. Examples of these are ethylenediaminetetramethylenephosphonic or -carboxylic acids or diethylenetriaminepentamethylenephosphonic acid or their salts.

Agents for adjusting the pH are employed for changing or maintaining the pH within the granules. Examples of these are citric acid, fatty acids or succinic acid or salts such as silicates, phosphates or sodium bisulfate.

Preparation

The imidoperoxycarboxylic acid and the granulating auxiliaries of the type a) and/or b) are mixed in a first step such that suitable granules are formed by agglomeration. This can be carried out in a kneader or mixer. The use of a kneader is appropriate wherever, owing to addition of a pasty granulating auxiliary, intensive mechanical mixing is necessary. If the mixing is carried out in a kneader, for example a Brabender kneader, it has proved advantageous also to additionally compress the material obtained in a granulator, for example a Eirich granulator. If inorganic, hydratable salts are used as granulating auxiliaries, it is advantageous to employ the imidoperoxycarboxylic acid with a water content of 50 to 5, preferably 35–20%. In this case, mixing can be carried out, for example, in a plowshare mixer from Lödige. The granules thus obtained require no further compaction after their drying. Customarily, granules having a granule size of 0.5 to 2 mm are aimed at. This can be achieved by sieving the granules. The amount of usable granules is in general 80%. The amounts lying above or below this can be fed back into the granulation process.

In a second step, the aqueous solution of the film-forming coating substance is sprayed onto the imidoperoxycarboxylic acid granules prepared in this way. In order to obtain a coating which is as complete as possible, the granules must be agitated during spraying. A particularly preferred form is therefore spraying in a fluidized bed. In this case, the coated granules can be simultaneously dried by warming the fluidizing air. The spraying is carried out in such a way that further agglomeration is prevented. Granule size and granule size distribution are therefore only insignificantly influenced by the coating process. Chelating agents, dyes and agents for regulating the pH can additionally also be dissolved in the aqueous polymer solution. The coated granules still have to be dried, depending on the spraying process.

The granules according to the invention are white, freeflowing granules having a bulk density between 500 and 1,200 kg/m$^3$, preferably between 550 and 1,100 kg/m$^3$.

Subsequent treatment, for example compression to give tablets or larger agglomerates, is possible and advantageous for particular application purposes.

Use

The granules according to the invention can generally be used wherever the imidoperoxycarboxylic acids are used as oxidants, bleaching agents and disinfectants. In particular, these granules can be employed in pulverulent detergents, cleaning agents and disinfectants. A further preferred field of application is found in the hygiene sector, for example as an additive to disinfectants or cleaning agents for hard surfaces, sanitary cleaners, dental hygiene agents, or cleaning salts. The dissolution rate of the peroxycarboxylic acid is not influenced or only insignificantly influenced by granulation. At 20° C., more than 70% of the available active oxygen for bleaching, oxidizing or disinfecting is available within 5 min. An effective action of the peracid is therefore achieved even at room temperature.

The granules can be formulated for this purpose with other solid active substances which are required in the corresponding field of application. In particular, it may be stressed that combinations with other bleaching agents such as persalts, persalt/activator systems or other peroxycarboxylic acids are also preferred in some cases.

Additional components which can be mentioned for use in detergents and cleaning agents are anionic, nonionic or cationic surfactants, builder systems on a zeolite, layer silicate or phosphate basis, co-builders, optical brighteners and perfume substances.

EXAMPLE 1

140 g of ε-phthalimidoperoxyhexanoic acid are kneaded at 100 revolutions per minute in a 0.3 l Brabender kneader with 47 g of sec. sodium alkanesulfonate (Hostapur ®SAS 60) for 5 minutes. The entire material from three kneader batches is then granulated at 900 revolutions per minute for 2 minutes in a 12 liter Eirich mixer granulator and subsequently dried in a vacuum drying oven at 40° C. to constant weight. After sieving, 85% of high-grade granules between 0.5 and 2.00 mm are obtained. 337 g of high-grade granules are initially introduced into a fluidized bed unit and fluidized by means of a stream of warm air at 40° C. flowing at about 50 m³/h. An aqueous 25.3% strength polyacrylic acid solution ($M_w \sim 15,000$ by GPC analysis), in which 0.24% of diethylenetriaminepentamethylenephosphonic acid (Dequest ® 2066 Monsanto) is dissolved, is simultaneously sprayed on by means of a nozzle situated at the bottom. 176 g of polyacrylic acid solution are sprayed onto the agitated granules in the course of 36 minutes. After drying in the vacuum drying oven at 40° C., 351 g of coated granules having the following composition result: 69% of ε-phthalimidoperoxyhexanoic acid (corresponding to an active oxygen content of the granules of 3.98%), 18% of secondary sodium alkanesulfonate (determined by two-phase titration according to Epton) and 11.8% of polyacrylic acid. The bulk density is 604 g/l.

Washing Tests

For the washing tests, ε-phthalimidoperoxyhexanoic acid (PAP) as a powder (contents: 96%) and the granules according to the invention in accordance with Example 1 above and also granules based on lauric acid were employed.

Granules 1: in accordance with Example 1: 69% PAP, 18% Na alkanesulfonate, 11.8% polyacrylic acid Granules 2: PAP granules not according to the invention based on lauric acid The washing tests were carried out in a Launder-O-Meter using the test stains tea on cotton (WFK) and red wine on cotton (EMPA, St. Gallen, CH). The water hardness was 15° dH. 1.5 g/l of phosphate-free standard detergent (WFK) were employed as a detergent. The amount of bleaching agent was selected such that theoretically 25 mg of active oxygen were available in each case per liter of washing liquor. The washing temperature was 20° C. and the washing period 30 min.

The bleaching power was determined as the increase in reflection of the various test fabrics. Evaluation was carried out in the usual way.

|  | Reflection [%] | |
|---|---|---|
|  | Tea | Red wine |
| Bleaching agent |  |  |
| PAP powder | 65.6 | 55.6 |
| Granules 1 | 64.9 | 54.9 |

|  | Reflection [%] | |
|---|---|---|
|  | Tea | Red wine |
| Granules 2 | 60.4 | 51.8 |

The washing results show that the active oxygen-releasing ability of the peroxycarboxylic acid is only slightly influenced at low temperature by granulation according to the invention. Granules 2 not according to the invention, on the other hand, lead to distinctly poorer bleaching results because of reduced cold water solubility.

Storage Tests

Determination of the Storage Stability 100 mg each of the granules according to Example 1 were mixed with 900 mg of phosphate-free standard detergent and the mixture was stored in open glass bottles at 20° C./60% atmospheric humidity, 38° C./30% atmospheric humidity and 38° C./80% atmospheric humidity. After one week in each case, the active oxygen content of an entire sample is determined and the result compared to the starting value.

Storage Stability

Degree of retention of the active oxygen in percent of the original content.

|  | Storage period/weeks | | | |
|---|---|---|---|---|
| Condition | 1 | 2 | 3 | 6 |
| 20° C./60% RH | 100 | 100 | 100 | 100 |
| 38° C./30% RH | 100 | 100 | 95 | 97 |
| 38° C./80% RH | 97 | 87 | 55 | 20 |

We claim:

1. A stable peroxycarboxylic acid granule, comprised of (a) 69 to 90% by weight of an imidoperoxycarboxylic acid or its salts of the formula

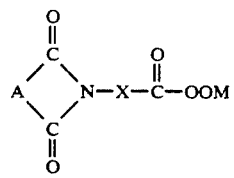

in which
A is a group of the formula

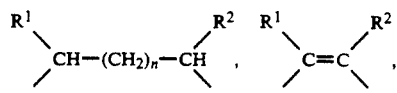

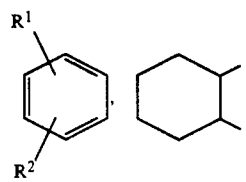

or

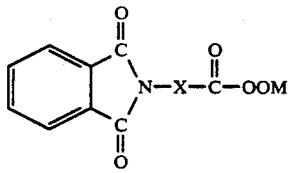

n is the number 0, 1 or 2.

$R^1$ is hydrogen, chlorine, bromine, $C_{14}$-$C_{20}$-alkyl, $C_1$-$C_{20}$-alkenyl, aryl, or alkylaryl, $R^2$ is hydrogen, chlorine, bromine or a group of the formula $-SO_3M$, $-CO_2M$ or $-OSO_3M$, M is hydrogen, alkali metal or ammonium ion or the equivalent of an alkaline earth metal ion, and X is $C_1$-$C_{19}$-alkylene, or arylene, (b) 5 to 39% by weight of granulating auxiliaries selected from the group consisting of an inorganic sulfate, phosphate salt, nonoxidizable surfactant, and mixtures thereof, and (c) 1 to 15% by weight of a film coating substance selected from the group consisting of a homo- or copolymer of units of acrylic acid, methacrylic acid, their salts, a copolymer of units of acrylic acid, methacrylic acid, their salts, mixtures thereof, and other carboxylic acids polymerizable therewith.

2. A stable peroxycarboxylic acid granule as claimed in claim 1, wherein, as a peroxycarboxylic acid, a compound of the formula

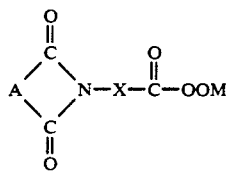

or its salts is employed, in which

A is a group of the formula $-CH_2-(CH_2)_n-CH_2-$, $-CH_2-CHR^1-$ or

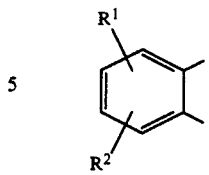

n is the number 0 or 1, $R^1$ is hydrogen, $C_1$-$C_{20}$-alkyl or $C_1$-$C_{20}$-alkenyl, $R^2$ is hydrogen or $CO_2M$ X is $C_3$-$C_{11}$-alkylene and M is hydrogen, an alkali metal or ammonium ion or the equivalent of an alkaline earth metal ion.

3. A stable peroxycarboxylic acid granule as claimed in claim 1, wherein polyacrylic acid or copolymers of acrylic acid or methacrylic acid with maleic acid, fumaric acid or itaconic acid are employed as the polymeric coating substance.

4. A stable peroxycarboxylic acid granule as claimed in claim 1, which additionally contains up to 3% a nonpolymeric chelate complex-forming substance to complex heavy metals.

5. A stable peroxycarboxylic acid granule as claimed in claim 1, wherein sodium sulfate, alkylbenzene sulfonate, alkanesulfonate or alkysulfate or mixtures thereof, are used as a granulating auxiliary.

6. A stable peroxycarboxylic acid granule as claimed in claim 1, wherein $R^1$ is phenyl.

7. A stable peroxycarboxylic acid granule as claimed in claim 1, wherein $R^1$ is $C_1$-$C_4$-alkylphenyl.

8. A stable peroxycarboxylic acid granule as claimed in claim 1, wherein X is $C_3$-$C_{11}$-alkylene or phenylene.

9. A stable peroxycarboxylic acid granule as claimed in claim 1, wherein the amount of granulating auxiliary in the finished granule is 15 to 35%.

10. A stable peroxycarboxylic acid granule as claimed in claim 1, wherein the amount of polymeric coating substance is 3 to 12%.

11. Bleaching agents, oxidants and disinfectants comprising granules as claimed in claim 1.

12. Detergents, cleaning agents and disinfectants comprising granules as claimed in claim 1.

* * * * *